(12) United States Patent
Mann et al.

(10) Patent No.: US 6,225,466 B1
(45) Date of Patent: May 1, 2001

(54) PHOTOCHROMIC SPIROFLUORENOPYRAN COMPOUNDS

(75) Inventors: Claudia Mann; Udo Weigand, both of Munich; Manfred Melzig, Wessling, all of (DE)

(73) Assignee: Optische Werke G. Rodenstock, Munich (DE)

( * ) Notice: Subject to any disclaimer, the term of this patent is extended or adjusted under 35 U.S.C. 154(b) by 0 days.

(21) Appl. No.: 09/321,746

(22) Filed: May 28, 1999

(30) Foreign Application Priority Data

May 29, 1998 (DE) .............................. 198 24 278
Jan. 25, 1999 (DE) .............................. 199 02 771

(51) Int. Cl.[7] ..................... C07D 295/02; C07D 307/94; C07D 311/96; C07D 413/02; C07D 453/00
(52) U.S. Cl. ............................. 544/70; 544/150; 546/94; 549/345; 549/428
(58) Field of Search .................... 549/345, 428; 544/70, 150; 546/94

(56) References Cited

U.S. PATENT DOCUMENTS

| | | | |
|---|---|---|---|
| 5,238,981 | * | 8/1993 | Knowles . |
| 5,645,767 | * | 7/1997 | Van Gement . |
| 5,698,141 | * | 12/1997 | Kumar . |
| 5,723,072 | * | 3/1998 | Kumar . |
| 6,113,814 | | 9/2000 | Gemert et al. .................... 252/586 |

* cited by examiner

*Primary Examiner*—Joseph K. McKane
*Assistant Examiner*—Taofiq A. Solola
(74) *Attorney, Agent, or Firm*—Evenson, McKeown, Edwards & Lenahan, P.L.L.C.

(57) ABSTRACT

Photochromic spirofluorenopyran compounds corresponding to the general formula (I):

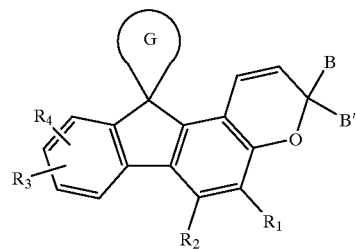

(I)

in which B, B', $R_1$ to $R_4$ and G have the meanings defined herein. The compounds of the invention are useful in the production of photochromic articles, particularly articles made of synthetic resin materials, and exhibit rapid darkening and brightening rates, as well as long useful service lives. By appropriate selection of substituents, it is possible to adjust the properties of the compounds such as absorption maxima (color), brightening rate, etc.

10 Claims, 7 Drawing Sheets

PHOTOCHROMIC SPIROFLUORENOPYRAN COMPOUNDS

BACKGROUND OF THE INVENTION

The invention relates to photochromic spirofluorenopyran compounds as well as to their use. The inventive compounds are photochromic pyran compounds, which are derived from 9H-fluorene, the carbon atom in the 9-position belonging to a further ring system and thus forming a spiro linkage site.

Certain classes of dyes have long been known which, when irradiated with light of particular wavelengths, especially with sunlight, reversibly change their color. This is due to the fact that these dye molecules are converted by light energy into an excited state, which they leave once again, returning to their initial state, when the supply of energy is interrupted. These photochromic dyes include different pyran systems, which already are described in the state of the art with different basic systems and substituents.

Pyrans, especially naphthopyrans and larger ring systems derived from these, are at the present time the class of photochromic compounds, on which most of the work has been done. Although the first patent application was filed as early as 1966 (U.S. Pat. No. 3,567,305), it was possible only in the 1990s to develop compounds, which appear to be suitable for use in eyeglasses. A suitable class of pyran compounds is, for example, the 2,2-diaryl-2H-naphtho(1,2-b)pyrans or the 3,3-diaryl-3H-naphtho(2,1-b)pyrans, which exhibit different colorations, such as yellow, orange or red-orange, in the excited state. A further class of photochromic compounds, which is of interest, is the indene-annelated naphthopyrans, which absorb at longer wavelengths because of their larger ring system. These can be systems, which are derived either from the 2H-naphtho(1,2-b)pyrans or the 3H-naphtho(2,1-b)pyrans, and are produced from the respective naphthopyran systems by the annelation at the f side of the naphthalene part.

Several publications are concerned with indene-annelated naphthopyrans derived from 2H-naphtho(1,2-b)pyrans. International Patent Application Nos. WO 97/48762 and WO 97/48993 and U.S. Pat. No. 5,723,072 describe naphthopyran compounds with a substituted or unsubstituted indeno group, the 2,1 positions of which are annelated with the f side of the naphthalene portion of a 2H-naphtho(1,2-b)pyran, the pyran ring having special substituents. In WO 97/48993 and U.S. Pat. No. 5,723,072, an unsubstituted, a monosubstituted or a disubstituted heterocyclic ring at the g, h, i, n, or p side of the indenonaphthopyran, can be annelated to this basic system. Accordingly, indeno(2,1-f)naphtho(1,2-b)pyrans with a very large variation of possible substituents are disclosed; however, ring formation between the substituents $R_1$ and $R_2$ at carbon atom No. 13 with formation of a spiro carbon atom is not described in these publications. A spiro linkage is disclosed only directly at the pyran ring at the substituents B and B'.

Published International Patent Application Nos. WO 96/14596 and WO 98/32037, International Patent Application No. PCT/DE 98/02820, and U.S. Pat. Nos. 5,645,767 and 5,698,141 also describe photochromic indene-annelated naphthopyran dyes, which are derived from 2H-naphtho(1,2-b)pyran, as well as the compositions containing them and a method for their synthesis. In U.S. Pat. No. 5,698,141, an unsubstituted, a monosubstituted or a disubstituted heterocyclic ring at the g, h, i, n, o or p side of the indenonaphthopyran can additionally be annelated to this basic system. Of the very extensive list of substituents, quite special spiro compounds have also been included, namely those systems with a spiro heterocyclic group, in which, including the spiro atom at the 13 position of the base system, a 5-membered to 8-membered ring, which always carries two oxygen atoms, is present.

The different known photochromic dyes are, however, associated with disadvantages which, when they are used in sunglasses, significantly affect the wearing comfort. The longwave absorption in the excited and in the unexcited state of the known dyes is inadequate. The temperature sensitivity of the darkening is too high and, at the same time, the brightening is frequently too slow. Moreover, the known dyes, and consequently the photochromic eyeglasses produced with them, frequently have an insufficient service life. Furthermore, a rapid decrease in performance and/or strong yellowing may be noted.

Moreover, the prior art includes hardly any references to the positions at which a pyran is to be substituted and to the substituents themselves, in order to achieve a particular longwave absorption maximum. In cases in which certain substitution patterns fix an absorption maximum, the kinetic properties, such as the darkening and brightening rates, the temperature dependence, etc. are also fixed therewith. Until now, it has not been possible to affect the kinetics at will in both directions, faster or slower, while having practically no effect on the absorption maximum.

SUMMARY OF THE INVENTION

It is therefore an object of the present invention to provide a new class of photochromic compounds which, relative to the structures described in the prior art, have clearly improved properties.

It is also an object of the invention to make it possible for those skilled in the art, by following appropriate selection rules for the particular application, to achieve tailor-made properties, such as the absorption maxima (color), brightening rate, etc.

These and other objects of the invention are achieved by the photochromic spirofluorenopyran compounds of formula (I):

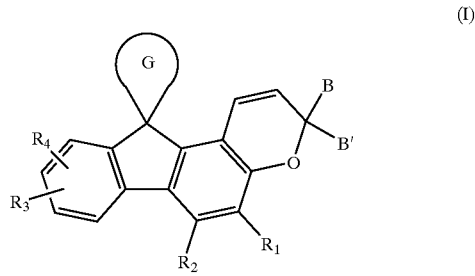

wherein
$R_1$ is a substituent, selected from the group A, comprising $C_1$ to $C_6$ alkyl, $C_1$ to $C_6$ alkoxy, phenyl, bromine, chlorine and fluorine, $R_2$, $R_3$ and $R_4$, independently of one another, are the same or different and represent a substituent, selected from group A', comprising hydrogen and the constituents of group A, or ($R_1$ together with $R_2$) and/or ($R_3$ together with $R_4$), independently of one another, represent an unsubstituted, monosubstituted or disubstituted benzene or pyridine ring, the substituents of which are selected from group A, G including the spiro carbon atom, represents a 5-membered to 8-membered ring, to which at least one aromatic or heteroaromatic ring is annelated, the ring system or systems being selected from group E, comprising benzene, naphthalene, phenanthrene, pyridine, quinoline, furan, thiophene, pyrrole, benzofuran, benzothiophene, indole and carbazol which, in turn, can have one or two substituents selected from group A, and B and B', independently of one another, are selected from the following groups a), b), c) or d) wherein
a) consists of the aryl groups phenyl and naphthyl, which are unsubstituted, monosubstituted, disubstituted and trisubstituted;
b) consists of the heterocyclic groups pyridyl, furanyl, benzofuranyl, thienyl, benzothienyl and julolidinyl, which are unsubstituted, monosubstituted or disubstituted,
the substituent or substituents of the aryl or heterocyclic groups in a) and b) being selected from the group F consisting of hydroxy, amino, $C_1$ to $C_6$ monoalkylamino, $C_1$ to $C_6$ dialkylamino, mono- and diphenylamino unsubstituted, monosubstituted or disubstituted at the phenyl ring, piperidinyl, N-substituted piperazinyl, pyrrolidinyl, imidazolidinyl, pyrazolidinyl, indolinyl, morpholinyl, carbazolyl, unsubstituted, monosubstituted and disubstituted pyrryl, $C_1$ to $C_6$ alkyl, $C_1$ to $C_6$ alkoxy, bromine, chlorine and fluorine, the substituent or substituents at the aromatic and heteroaromatic rings being selected from the group consisting of $C_1$ to $C_6$ alkyl, $C_1$ to $C_6$ alkoxy, bromine, chlorine and fluorine; or
c) consisting of the groups having the following structures:

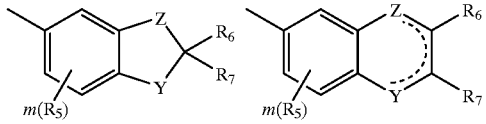

wherein
Y and Z, independently of one another, are selected from the group, consisting of O, S, CH, $CH_2$, $NR^N$ in which the nitrogen substituents $R^N$ are selected from $C_1$ to $C_6$ alkyl, $C_1$ to $C_6$ acyl, phenyl and hydrogen, and
the substituents $R_5$ are selected from group A and hydroxy, m represents 0, 1 or 2, and
$R_6$ and $R_7$, independently of one another, are hydrogen and/or $C_1$ to $C_6$ alkyl, or
d) consists of B and B' together representing unsubstituted, monosubstituted or disubstituted fluorene-9-ylides or a saturated hydrocarbon, which is $C_3$ to $C_{12}$ spiro monocyclic, $C_7$ to $C_{12}$ Spiro bicyclic and/or $C_7$ to $C_{12}$ spiro tricyclic, the fluorene substituents being selected from group A.

Accordingly, the ring system G, including the Spiro carbon atom, represents a 5-membered to 8-membered ring. To this ring at least one aromatic or heteroaromatic ring system is annelated. In accordance with the invention, the annelated ring system or systems can be selected independently of one another from the group consisting of benzene, naphthalene, phenanthrene, pyridine, quinoline, furan, thiophene, pyrrole, benzofuran, benzothiophene, indole and carbazole. Of course, the ring systems can be unsubstituted, monosubstituted or disubstituted, the substituent or substituents, if any, being selected from the group A defined above.

In the present invention, $C_3$ to $C_{12}$ spiro monocyclic is defined as a 3-membered to 12-membered ring, which is known to those skilled in the art. The $C_7$ to $C_{12}$ spiro bicyclic systems, which may be present pursuant to the invention, also are a part of the general knowledge of an expert. Norbornane, norbornene, 2,5-norbornadiene, norcaran and pinan are named by way of example. Adamantane, for example, is a known Spiro tricyclic system, which can be used in the invention.

The invention also relates to photochromic spirofluorenopyran compounds corresponding to the general formula (II):

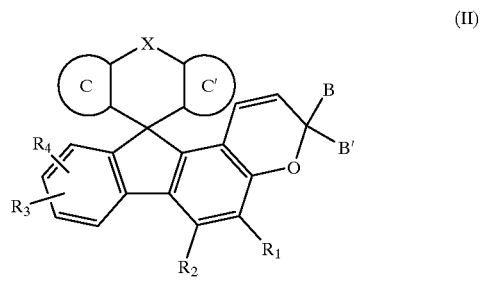

wherein
$R_1$ to $R_4$, B and B' are described as above;
X either is a single bond or selected from the group comprising
—O—, —S—, —$(CR_2)_{n-}$ with n=1, 2 or 3,
D=D'— with D,D'=N,CR or
LL' with L,L'=O,S,NR,CHR or $CR_2$,
wherein R=H, $C_1$ to $C_6$ alkyl or phenyl and L and L' cannot both be O or S at the same time, and
C and C', independently of one another, are selected from the above-defined group E and, in each case, can have one or two substituents selected from group A.

If X is described as a "single bond" in the present invention, then this means that there is a direct bond between, for example, the ring systems C and C', which are to be linked, and that there is no other atom involved in the bridging.

According to a further, preferred embodiment of the invention, X represents a single bond, the two ring systems C and C' present being bridged by a further linkage between the positions ortho and ortho' to the first linkage. Such a bridging includes every possibility, known to those skilled in the art of linking the two ring systems C and C', for example, by hetero atoms, such as oxygen or sulfur, saturated or unsaturated $C_2$ to $C_5$ carbon chains or the like. For example, the further linkage in the ortho and ortho' positions can lead to a 4,5-phenanthryl spiro compound, in which case the inventive spiro compounds can then have the following general structure (III):

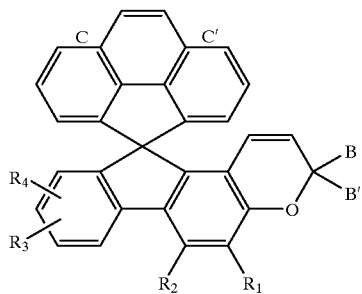

(III)

It may also be of advantage if, in the inventive spiro compounds, B and B' are selected independently of one another from group a) or group d). It is particularly advantageous if B and B', independently of one another, represent unsubstituted or monosubstituted phenyl or naphthyl, the substituent being selected in each case from the group F, defined above. In the inventive, photochromic Spiro compounds, B and B' can also be the same substituents.

According to a further preferred embodiment of the invention, C and C', independently of one another, are unsubstituted or monosubstituted phenyl or naphthyl, the substituent in each case being selected from group A. C and C' can also represent the same substituents.

The following inventive photochromic spirofluorenopyrans have particularly advantageous properties:

1) spiro-9-fluorene-13'-(3,3-diphenyl-6-methoxy-indeno (2,1-f)naphtho(1,2-b)pyran);
2) spiro-9-fluorene-13'-(6-methoxy-3-(4-methoxyphenyl)-3-phenyl-indeno(2,1-f)-naphtho(1,2-b)pyran);
3) spiro-9-xanthene-13'-(6-methoxy-3-(4-methoxyphenyl)-3-phenyl-indeno(2,1-f)-naphtho(1,2-b)pyran);
4) spiro-9-fluorene-13'-(3,3-bis(4-methoxyphenyl)-6-methoxy-indeno(2,1-f)naphtho-(1,2-b)pyran);
5) spiro-9-xanthene-13'-(3,3-bis(4-methoxyphenyl)-6-methoxy-indeno(2,1-f)-naphtho(1,2-b)pyran);
6) spiro-9-(9,10-dihydroanthracene)-13'-(3,3-bis(4-methoxyphenyl)-6-methoxy-indeno(2,1-f)naphtho(1,2-b)pyran);
7) spiro-9-fluorene-13'-(6-methoxy-3-(4-N-morpholinyl) phenyl)-3-phenyl-indeno(2,1-f)-naphtho(1,2-b)pyran);
8) spiro-9-fluorene-13'-(3-(4dimethylaminophenyl)-6-methoxy-3-phenyl-indeno(2,1-f)-naphtho(1,2-b) pyran);
9) spiro-9-fluorene-13'-(3-(4-dimethylaminophenyl)-6-methoxy-3-phenyl-indeno(2,1-f)-naphtho(1,2-b) pyran);
10) spiro-9-fluorene-13'(3,3-bis(4-methoxyphenyl)-indeno(2,1-f)naphtho(1,2-b)pyran);
11) spiro-9-fluorene-13'-(3-(4-(N-morpholinyl)phenyl)-3-phenyl-indeno(2,1-f)naphtho-(1,2-b)pyran);
12) spiro-9-fluorene-11'-(3,3-bis(4-methoxyphenyl)-5-bromo-fluoreno(2,1 -b)pyran) or
13) spiro-9-fluorene-13'-(3,3-bis(4-methoxyphenyl)-5-bromo-benzo(I)fluoreno(2,1-b)pyran).

The invention further relates to the use of one or more of the photochromic spirofluorenopyrans in synthetic resins of all types, especially for ophthalmic purposes. For example, the inventive photochromic dyes can be used in lenses, glasses, for spectacles of all types, such as ski goggles, sunglasses, motorcycle goggles, helmet visors and the like. In particular, the inventive spirofluorenopyrans can also be used for protection against the sun in vehicles, in residences in the form of windows, protective shades, coverings, roofs or the like.

The inventive compounds are distinguished by a plurality of advantages. They are a completely novel class of photochromic compounds, which do not have the disadvantages of the compounds known in the art. Surprisingly, it was possible to overcome the aforementioned problems of the compounds of the state of the art by the inventive Spiro compounds, that is, by linking the substituents, usually free at the central carbon atom of the fluorene structure, into a closed ring system, at least one aromatic and/or heteroaromatic system being present as an additional component of the new ring. The closest compounds, described in the state of the art, are the indene-annelated naphthopyrans, which are disclosed in the PCT/DE 98/02820. Knowing the present invention, compounds in the form of so-called "carbinols" can be derived from these naphthopyrans. Compared to the closest known compounds as well as to the derived compounds, it was possible to achieve a desirable effect on the brightening and substantial improvements in the service life with the inventive spiro compounds. A yellowing, which is observed with the carbinols, no longer occurs with the inventive Spiro compounds. At the same time, it was completely unexpected that, despite the electronic decoupling of the new inventive structure parts from the color center, a different, much clearer color effect results in the excited state.

All of these inventive spiro compounds are accordingly distinguished from the closest state of the art by a better aging behavior with respect to maintaining performance as well as color. Since these closest compounds belong to the class of indene-annelated naphthopyrans, this state of the art was acknowledged particularly.

BRIEF DESCRIPTION OF THE DRAWINGS

The invention will be explained in further detail hereinafter with reference to the accompanying drawing figures in which.

DESCRIPTION OF ILLUSTRATIVE EMBODIMENTS

Figure 1:
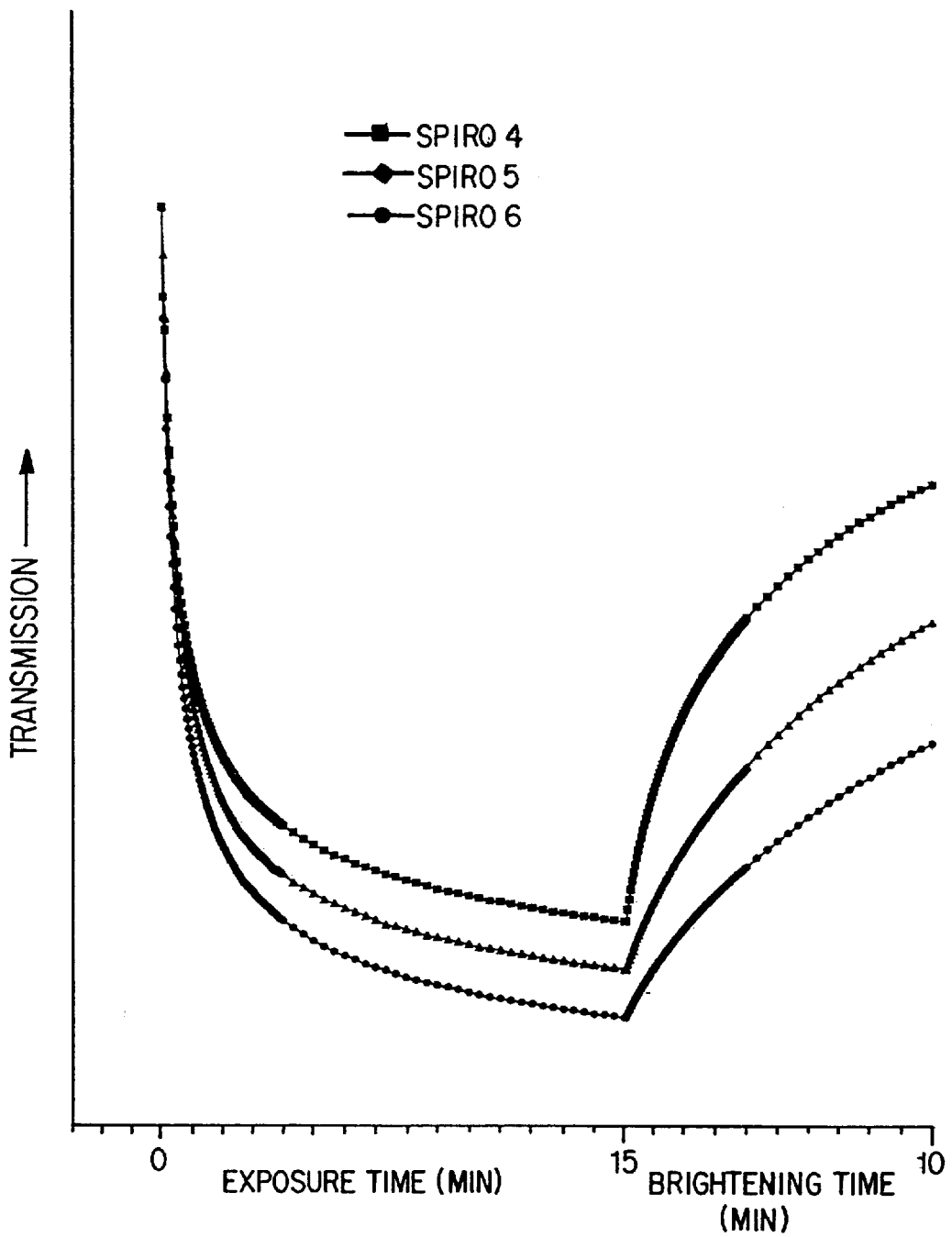
FIG. 1 is a graph of the darkening and brightening rates of test compounds.

Properties of the inventive spiro compounds are explained in further detail hereinafter with reference to some illustrative test compounds. It is to be understood, of course, that the invention is not limited to these embodiments. Brightening Rate and the Longest Wavelength Absorption Maxima $\lambda_{max}$ The effect of the substituents $R'_1$ to $R'_3$ on the brightening rate within 10 minutes/ $(\tau_0 - \tau_s)$ $(\Delta_{10\,min} = ((\tau_{10\,min} - \tau_s)))$ and on the longest wavelength absorption maxima $\lambda_{max}$ of the inventive spiro compounds (X=single bond) was investigated. The formulas of the chemical structures of the spiro and carbinol compounds used are shown below, $R_1'$ either being hydrogen or selected from group A, $R_2'$ and $R_3'$, independently of one another, being hydrogen or selected from group F and $R_4'$ being selected in such a manner that the corresponding spiro compounds results from cyclizing.

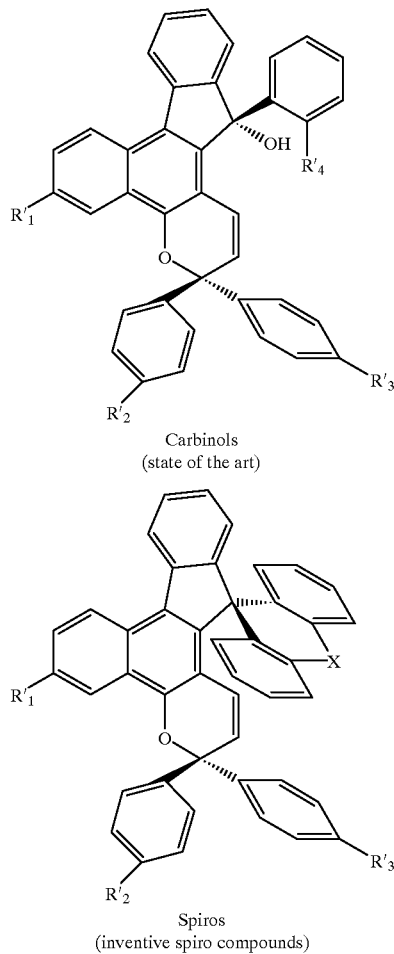

Carbinols
(state of the art)

Spiros
(inventive spiro compounds)

The results of the measurements are given in Table 1.

TABLE 1

| $R'_1$ | $R'_2$ | $R'_3$ | Example | $\Delta_{10\ min}$ | $\lambda_{max}$ |
|---|---|---|---|---|---|
| A) Substituent $R'_1$ | | | | | |
| H | OMe | OMe | Spiro 10 | 54% | 550 nm |
| OMe | OMe | OMe | Spiro 4 | 49% | 575 nm |
| H | Morph | H | Spiro 11 | 44% | 575 nm |
| OMe | Morph | H | Spiro 7 | 43% | 595 nm |
| B) Substituent $R'_2$ | | | | | |
| OMe | H | H | Spiro 1 | 29% | 555 nm |
| OMe | OMe | H | Spiro 2 | 37% | 565 nm |
| OMe | Morph | H | Spiro 7 | 43% | 595 nm |
| OMe | $NPh_2$ | H | Spiro 9 | 33% | 600 nm |
| OMe | $NMe_2$ | H | Spiro 8 | 51% | 615 nm |
| C) Substituent $R'_3$ | | | | | |
| OMe | OMe | H | Spiro 2 | 37% | 565 nm |
| OMe | OMe | OMe | Spiro 4 | 49% | 575 nm |

For the sake of greater clarity, the inventive compounds have been abbreviated by "spiro", the subsequent number referring directly to the corresponding example, in which the synthesis of this compound is described.

It can be seen from Table 1 that an electron donor substituent at $R'_1$ ($OCH_3$ instead of H) results in a bathochromic shift in the $\lambda_{max}$ by 20 to 25 nm, the brightening rate remaining about the same. The same substitution at $R'_2$ leads to a bathochromic shift of only 10 nm. At the same time, the brightening rate increases by almost 30%. If the electron donor effect of the substituent is greater, the bathochromic shift of the $\lambda_{max}$ can be as high as 50 nm. A further $OCH_3$ group instead of H at $R'_3$ results once again in a further bathochromic shift by 10 nm and an increase in the brightening rate of more than 30%. As shown, the longest wavelength absorption maxima, as well as the brightening rate, can be tailored within a very wide range to the particular application by selecting suitable substituents $R'_1$ to $R'_3$.

In the following, the effect of the spiro linkage on the brightening rate within 10 minutes ($\Delta_{10\ min}=((\tau_{10\ min}-\tau_s)/(\tau_0-\tau_s))$) and on the longest wavelength absorption maxima $\lambda_{max}$ was investigated. The data obtained from the carbinol compounds and the corresponding inventive spiro compounds were compared. The results obtained are given in Table 2.

TABLE 2

| $R'_1$ | $R'_2$ | $R'_3$ | $R'_4$ | X | Example | $\Delta_{10\ min}$ | $\lambda_{max}$ |
|---|---|---|---|---|---|---|---|
| OMe | H | H | Ph | | Carbinol 1 | 22% | 560 nm |
| OMe | H | H | | —* | Spiro 1 | 29% | 555 nm |
| OMe | OMe | H | Ph | | Carbinol 2 | 26% | 575 nm |
| OMe | OMe | H | | — | Spiro 2 | 37% | 565 nm |
| OMe | OMe | H | OPh | | Carbinol 3 | 25% | 575 nm |
| OMe | OMe | H | | O | Spiro 3 | 26% | 565 nm |
| OMe | OMe | OMe | Ph | | Carbinol 4 | 36% | 585 nm |
| OMe | OMe | OMe | | O | Spiro 4 | 49% | 575 nm |
| OMe | OMe | OMe | Ph | | Carbinol 5 | 35% | 585 nm |
| OMe | OMe | OMe | | O | Spiro 5 | 35% | 575 nm |
| OMe | OMe | OMe | $CH_2Ph$ | | Carbinol 6 | 44% | 580 nm |
| OMe | OMe | OMe | | $CH_2$ | Spiro 6 | 29% | 575 nm |
| OMe | Morph | H | Ph | | Carbinol 7 | 25% | 600 nm |
| OMe | Morph | H | | — | Spiro 7 | 43% | 595 mn |

*"—" means that X represents a single bond.

For the sake of greater clarity, the compounds, based on the state of the art, are abbreviated by "carbinol" in Table 2, the subsequent number referring directly to the corresponding example, in which the synthesis of this compound is described.

As can be seen from Table 2, the effect of the spiro linkage on the longest wavelength absorption maxima is very slight. Compared to the carbinol starting compounds of a similar structure, there is merely a hypsochromic shift by 5 to 10 nm. On the other hand, the brightening rate can be affected as desired by the type of spiro linkage. A direct linkage accelerates, an oxygen bridge has no effect on and a methylene bridge retards the brightening rate.

This is shown graphically in FIG. 1 for the spiro compounds spiro 4–6. The measurements were carried out at 23° C., 15 minutes illumination at 50 klux and 10 minutes dark brightening. To make the comparison easier, the different transmission values after 15 minutes of illumination were converted to equal intervals.

After the other properties of the photochromic compounds (such as the absorption behavior, the migration behavior, the affinity for the polymer matrix) are adapted with the inventive teachings to values optimum for the particular application with the help of $R'_1$ to $R'_3$, it is now possible to adapt, as desired, the kinetics, that is, the brightening rate and, with that, the temperature dependence of the photochromic reaction, by means of $R'_4$. When selecting the color, only the slight hypsochromic shift resulting from the spiro linkage must be taken into consideration from the very start when selecting $R'_1$ to $R'_3$.

This completely surprising effect of the different spiro linkage bridges of the inventive spiro compounds could not have been anticipated any more than the greatly improved behavior in the service life test.

Yellow Index Increase Δyi and Performance Retention LE in the Service Life Test

Furthermore, the increase in the yellow index Δyi as well as the performance retention LE in the service life test (50 h xenon lamp) were determined. The following relationship applies:

$$\Delta yi = yi_{after\ 50\ hours\ xenon\ test} - yi_{before\ xenon\ test}$$
$$LE = (\tau_{S\ before\ xenon\ test}/\tau_{S\ after\ 50\ hours\ xenon\ test})$$

The formulas of the chemical structures of the compounds used are shown in the following.

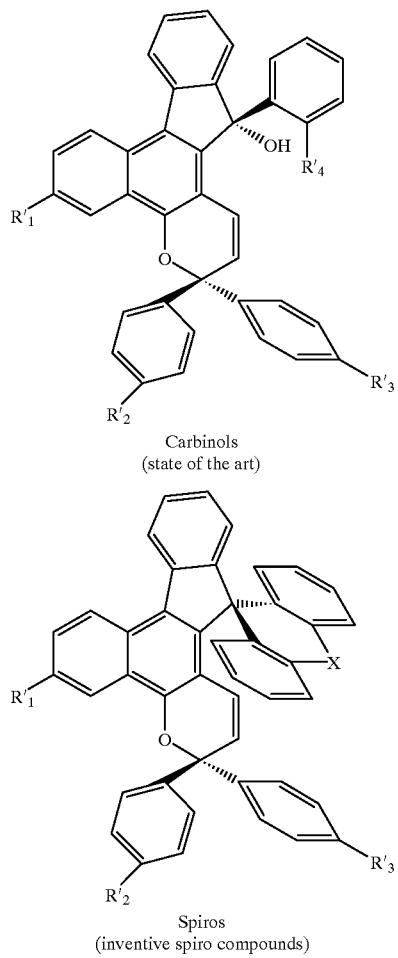

Carbinols
(state of the art)

Spiros
(inventive spiro compounds)

The results of the measurements are given in Table 3.

TABLE 3

| R'$_1$ | R'$_2$ | R'$_3$ | R'$_4$ | X | Example | Δyi | LE |
|---|---|---|---|---|---|---|---|
| OMe | H | H | Ph |  | Carbinol 1 | 7.22 | 89% |
| OMe | H | H |  | —* | Spiro 1 | -0.10 | 90% |
| OMe | OMe | H | Ph |  | Carbinol 2 | 15.82 | 85% |
| OMe | OMe | H |  | — | Spiro 2 | 1.68 | 89% |
| OMe | OMe | H | OPh |  | Carbinol 3 | 3.46 | 92% |
| OMe | OMe | H |  | O | Spiro 3 | -0.57 | 90% |
| OMe | OMe | OMe | Ph |  | Carbinol 4 | 29.86 | 77% |
| OMe | OMe | OMe |  | O | Spiro 4 | -0.97 | 98% |

TABLE 3-continued

| R'$_1$ | R'$_2$ | R'$_3$ | R'$_4$ | X | Example | Δyi | LE |
|---|---|---|---|---|---|---|---|
| OMe | OMe | OMe | Ph |  | Carbinol 5 | 6.75 | 86% |
| OMe | OMe | OMe |  | O | Spiro 5 | -2.29 | 85% |
| OMe | OMe | OMe | CH$_2$Ph |  | Carbinol 6 | 32.34 | 81% |
| OMe | OMe | OMe |  | CH$_2$ | Spiro 6 | -1.92 | 98% |
| OMe | Morph | H | Ph |  | Carbinol 7 | 19.69 | 80% |
| OMe | Morph | H |  | — | Spiro 7 | 0.25 | 89% |

*"—" means that X represents a single bond.

Compared to the corresponding carbinol compounds, which are structurally somewhat similar to the state of the art, a better retention of the photochromic performance is achieved in general with the inventive spiro compounds. In a particular case, such as examples 4 and 6, the loss in performance after 50 hours of xenon test is only 2% for the spiro compounds, but 20% for the carbinols. In prolonged use in ophthalmic glasses, the user can therefore expect to wear the eyeglasses with the inventive compounds several times as long.

Even more dramatic and also completely surprising is the decrease in the yellow index change in the fully darkened state after 50 hours of xenon test in all cases. This was not to be expected and can also not be attributed to the absence of the hydroxy group in the spiro compound, since some carbinols show only a slight (No. 3), while others show an extreme change in the yellow index (No. 6).

Figure 2:
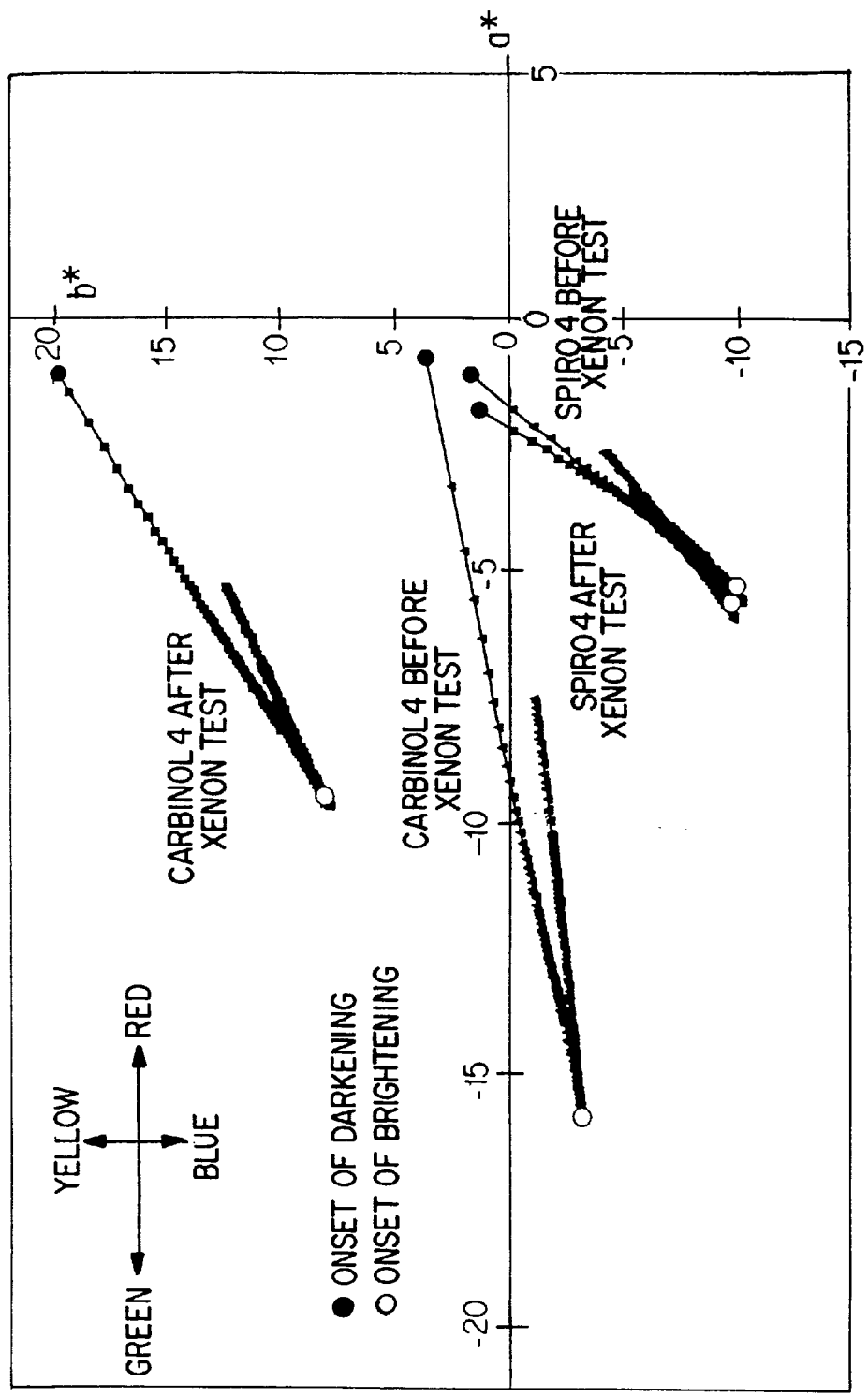
FIGS. 2, 3 and 4 are graphs of a*/b* chromaticity curves of three sets of test of compounds at 23° C. before and after xenon lamp exposure for 15 minutes at 50 klux, with 10 minutes brightening time under dark conditions.
Figure 3:
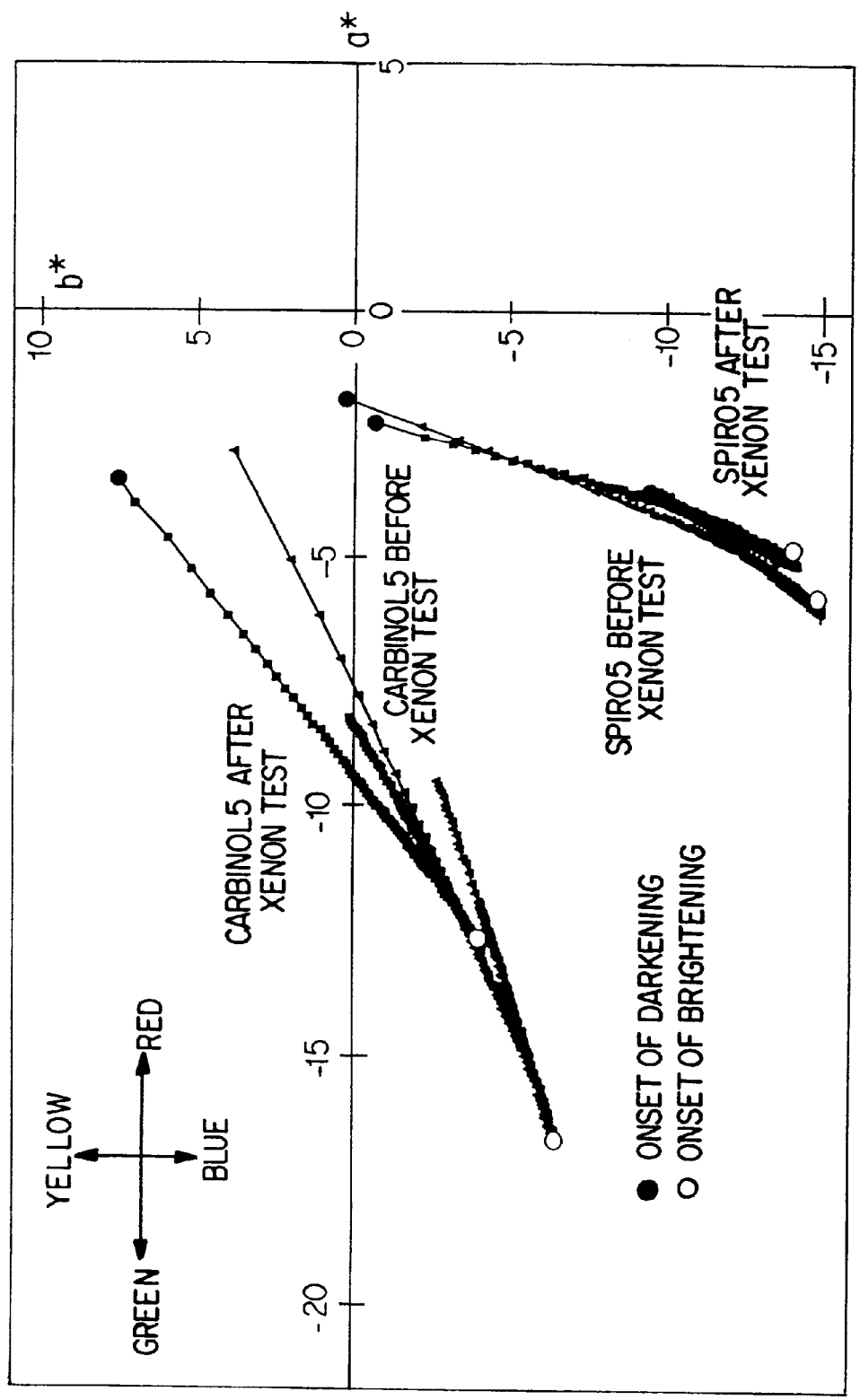
Figure 4:
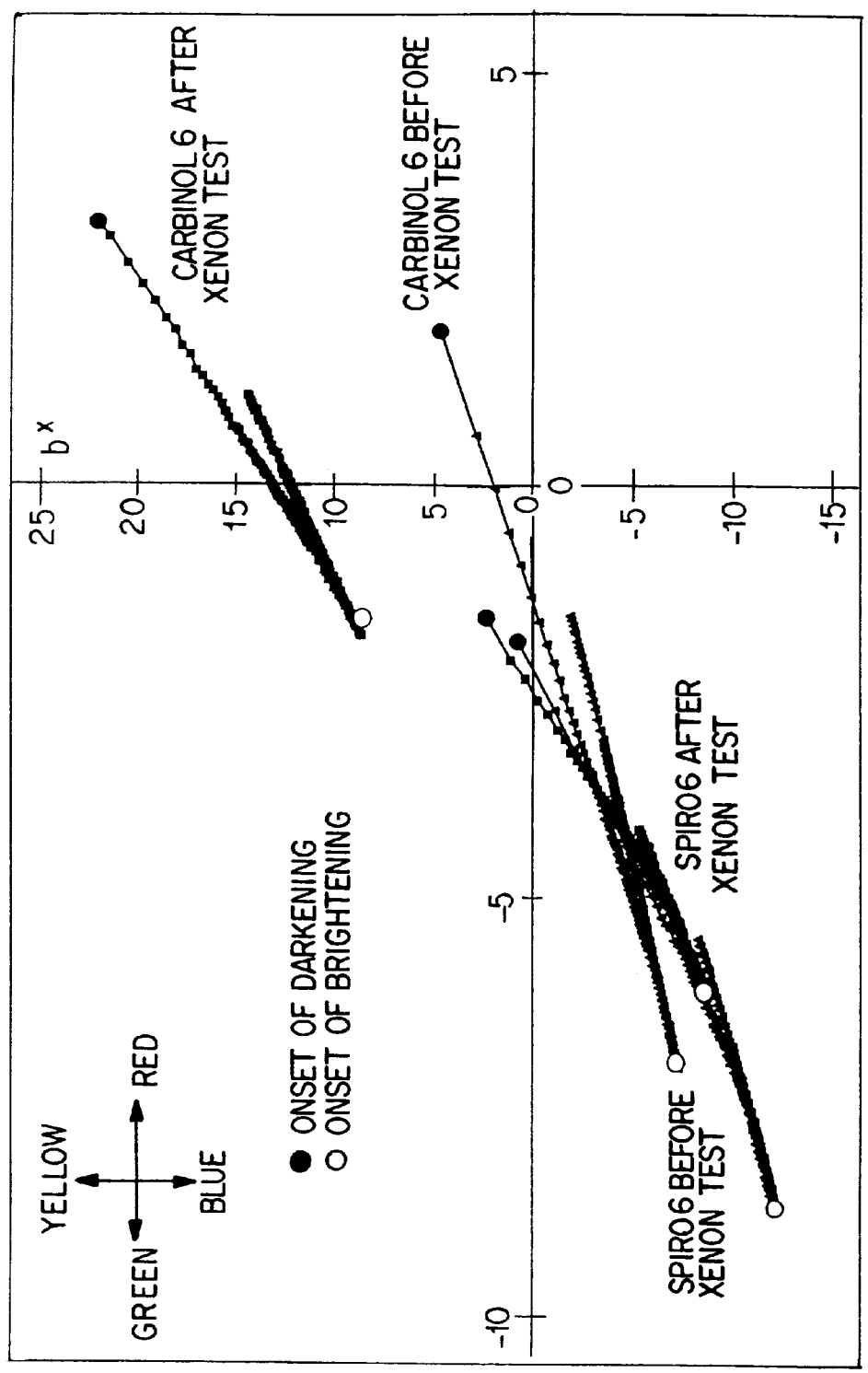
Figure 5A:
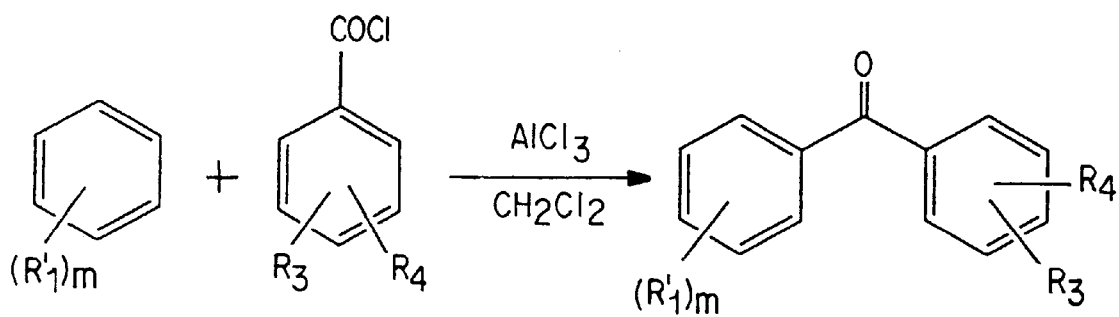
FIGS. 5 and 6 are representations of synthesis schemes for producing the spirofluorenopyran compounds of the invention.
Figure 5B:
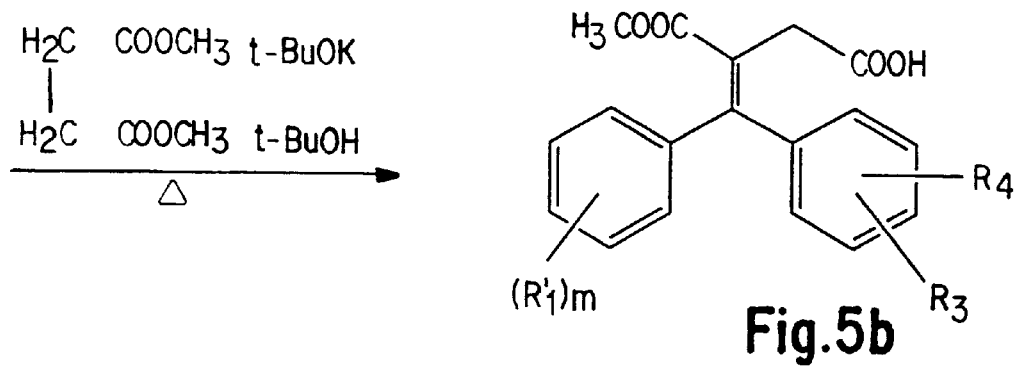
Figure 5C:
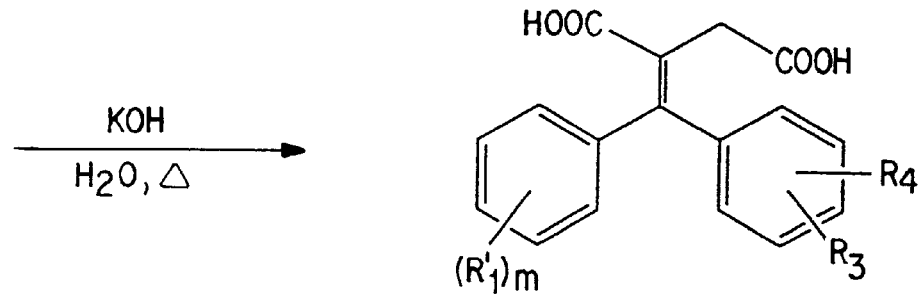
Figure 5D:
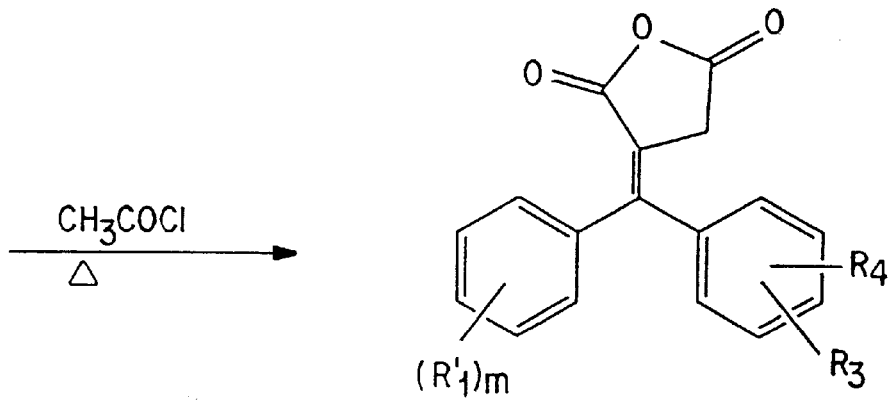
Figure 5E:
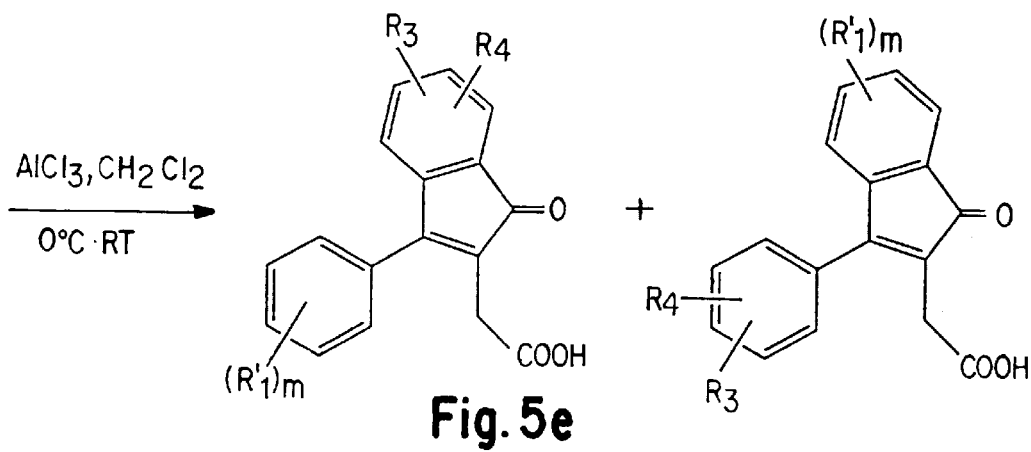
Figure 5F:
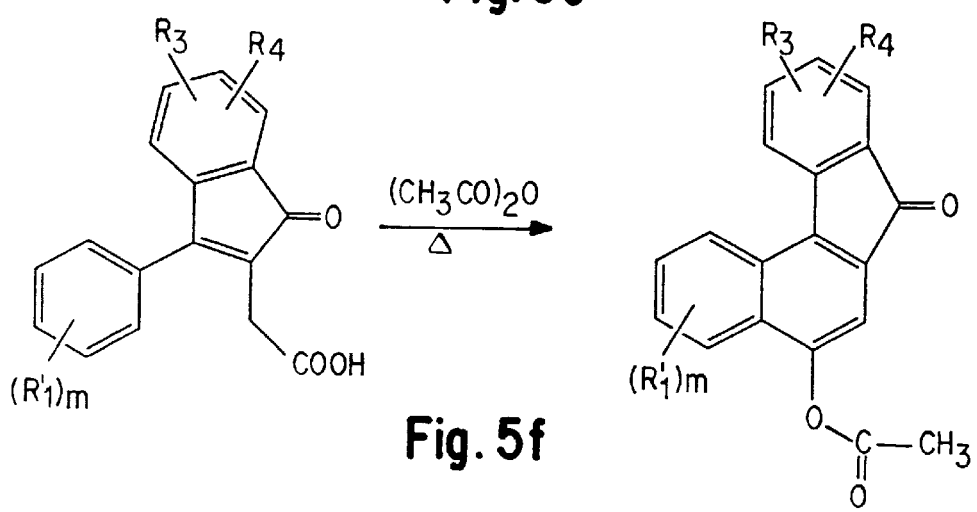
Figure 5G:
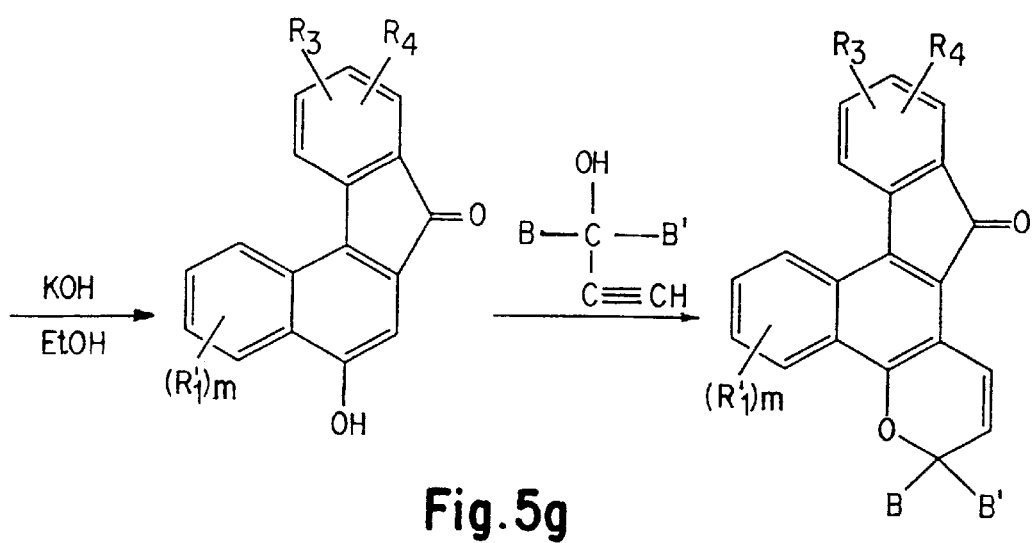

In the FIGS. 2, 3 and 4, the a*/b* chromaticity curves of three carbinol compounds and spiro compounds before and after the 50-hour xenon test are shown. The measurements were conducted at 23 ° C., 15 minutes illumination, at 50 klux and 10 minutes dark brightening. It can be seen clearly here that the chromaticity of the carbinols is shifted dramatically during the course of a darkening and brightening cycle by the aging, while the corresponding spiro compounds remain true to color over the aging period. This is confirmed impressively by the position of the measurement curves of the carbinol and spiro compounds before and after the xenon aging test.

Two states are of particular importance to those who wear glasses: the brightened state and the fully darkened state. In contrast to the intermediate states, these are experienced in a quasi stationary fashion. In comparison to the corresponding carbinols, all three examples of bridge systems of the inventive spiro bridging show practically no tendency to age. For use in spectacles, this is even more important than the strict retention of performance, since experience has shown that those, who wear glasses, do not notice a slight reduction in the darkening performance during prolonged use. On the other hand, a slight color change is noted quickly and regarded as a deficiency.

Figure 6A:
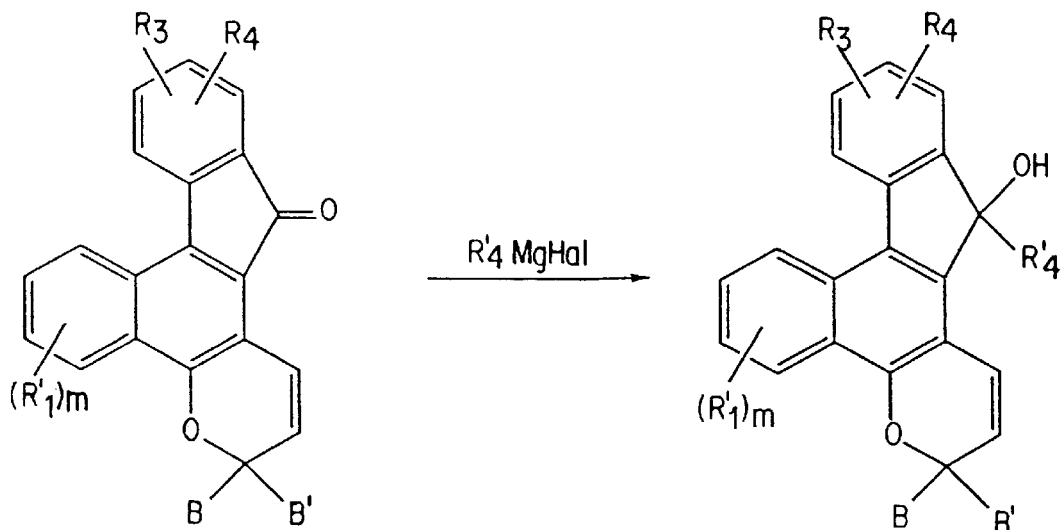
Figure 6B:
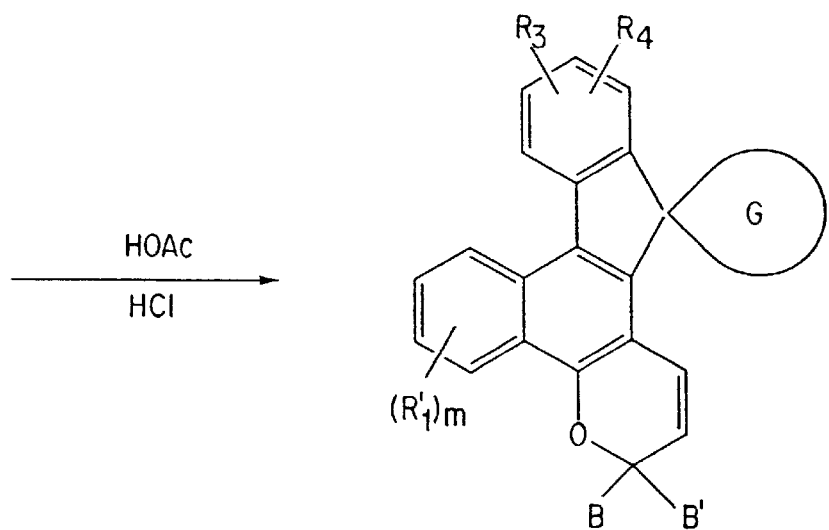

In the following, the preparation of the inventive spiro compounds is explained by means of a general synthesis path. For this purpose, reference is made to the general synthesis outline, which is shown in FIGS. 5 and 6.

The substituted or unsubstituted benzophenones and naphthophenones (a), used as starting material, either are obtainable commercially or can be obtained easily and generally in good yield by the Friedel-Crafts acylation of step (1). The groups R$_3$ and R$_4$ correspond here to the substituents already defined above. (R$_1$')$_m$ is selected from group A with m=0, 1 or 2.

In step (2), the half ester (b) is produced by the Stobbe condensation using the diester of succinic acid. If the two rings, linked over the keto group, are not identical, a mixture of isomers is formed. Deviating from the synthesis in WO 96/14596, further work is carried out in the present invention with the isomer mixture. The separation of the honey-like isomers, which generally do not crystallize, requires much effort and, for the synthesis path selected for the invention, can be a carried out very easily later on. Subsequently, the mixture of half esters is saponified with aqueous alkali in accordance with step (3) to the mixture of isomeric diacids (c). By heating with acetyl chloride in step (4) and splitting off the water, the mixture of isomeric cyclic anhydrides (d) is then produced.

In step (5), the isomer mixture (e) is synthesized with aluminum chloride by intramolecular 5-ring cyclization. These compounds crystallize very well and in most cases, due to their different solubility in benzene, can easily be separated into the two isomers. The ester (f) is formed from the desired isomer by intramolecular six-ring cyclization under the influence of acetic anhydride in accordance with step (6). This ester is subsequently saponified in step (7) under alkaline conditions to the hydroxyfluorenone derivative (g).

The reaction with a 2-propin-1-ol derivative (step (8)), in which B and B' are defined as above, leads to the indene-annelated naphthopyrans (h), which are weakly photochromic and colored a dark red. This reaction is not described in greater detail here, since it can be carried out similarly to the reaction with 1- or 2-naphthols. Examples in connection with this may be found, for example, in U.S. Pat. Nos. 5,066,818 and 5,238,981 and European patent EP 246,114. With appropriate Grignard compounds, the compounds (i), referred to in the present invention as so-called carbinols, are formed in step (9), R'$_4$ being selected so that the corresponding spiro compounds with the above-defined G ring can be formed. The free hydroxyl group in (i) is subsequently cyclized in step (10) with acetic acid/hydrochloric acid to the corresponding spiro compounds.

Compared to the synthesis method recommended in WO 96/14596 or in the U.S. Pat. No. 5,605,767, the synthesis above has various advantages:

On one hand, various compounds cannot be synthesized by the method described in WO 96/1596 or the U.S. Pat. No. 5,605,767. The method described above is significantly more gentle. For example, the one-hour heating with concentrated phosphoric acid to a temperature higher than 190° C. is omitted. As a result, more sensitive groupings can also be used as substituents. The closing of the 5-membered before the 6-membered ring in the above method also frequently leads to products, which cannot be synthesized or can be synthesized only with difficulty by the method of the state of the art—closing the 6-membered ring before the 5-membered ring. On the other hand, with the same target product and, for example, symmetrical benzophenones as starting material, fewer by-products are formed by the method described above and the photochromic dyes are purified more easily and obtained in higher yields. The exact synthetic method is described in detail for the synthesis of the following examples. Of course, these examples do not limit the range of protection of the present invention and are intended only for purposes of illustration.

EXAMPLE 1

Steps i) to vi) of this example were carried out, with some modifications, on the basis of the article published by F. G. Baddar, L. S. El-Assai and V. B. Baghos in the J. Chem. Soc. 1958, pages 986 ff.

i) t-butanol is initially melted in a warm water bath. Potassium t-butylate (30 g) is suspended in 600 ml of t-butanol and 4-methoxybenzophenone (50 g) in a 1 liter 3-neck flask and dimethyl succinate (45 g) is added. The mixture is stirred well and refluxed for one hour. After that, potassium t-butylate (30 g) and dimethyl succinate (30 g) are added once again and refluxed for two hours. After cooling, the product is hydrolyzed with a total of 2liters of water and then, while being stirred, acidified with concentrated hydrochloric acid. Subsequently, it is extracted twice with 400 ml of ether and the combined ether phases are washed once with 400 ml of water. The ether solution is then extracted twice with 500 ml of saturated sodium hydrogen carbonate solution. The product, as carboxylate, goes into the aqueous phase, which is washed once with 200 ml of ether and subsequently, while being stirred, acidified in a large beaker with concentrated hydrochloric acid. Subsequently, the aqueous phase is extracted twice with 400 ml of ether and the organic phase is washed once with water. After drying over sodium sulfate, the ether is evaporated in a rotary evaporator. The orange yellow, honey-like reaction product (75 g) was identified by nuclear magnetic resonance (NMR) as 3-methoxycarbonyl-4-(4-methoxyphenyl)4-phenyl-3-butenoic acid.

ii) In a one liter flask, the above reaction product is dissolved in a solution of potassium hydroxide (40 g) in about 600 ml of water. The brown reaction solution formed is heated for 3 hours under reflux. After cooling, the solution is stirred, cooled well in an ice bath and acidified with concentrated hydrochloric acid. Subsequently, it is extracted twice with 400 ml of ethyl acetate. The combined ester phases are washed once with water and, after being dried over sodium sulfate, evaporated to dryness in a rotary evaporator. The honey-like reaction product (70 g) was identified by NMR as being 3-carboxyl-4-(4-methoxyphenyl)-4-phenyl-3-butenoic acid.

iii) The above reaction product is dissolved with 35 g of acetyl chloride in 300 ml of acetic acid, stirred and refluxed for 2 hours. After the solvent is distilled off, the residue, while still warm, is dissolved in about 600 ml of ethyl acetate and extracted twice with water. Subsequently, it is extracted twice with 300 ml of a 5% sodium carbonate solution. The organic phase is washed once again with water, dried over sodium sulfate and evaporated to dryness in a rotary evaporator. The reaction product (60 g) is obtained as a dark, viscous oil and was identified by NMR as (4-methoxyphenyl-phenyl-methylene)succinic anhydride.

iv) The above reaction product is dissolved at room temperature in about 600 ml of dichloromethane and subsequently well cooled in an ice bath. Subsequently, it is stirred and cooled well and aluminum chloride (35 g) is added in portions and the mixture is allowed to thaw overnight. After that, the reaction mixture is poured into one liter of ice/water in order to hydrolyze it. After the organic phase is separated, it is washed twice with 500 ml of water and subsequently extracted twice with 600 ml of 5% sodium bicarbonate solution. After the combined aqueous alkaline phases are washed with 250 ml of ether, they are acidified with concentrated hydrochloric with stirring and extracted twice with 400 ml of ethyl acetate. The organic phase is then washed with water, dried over sodium sulfate and evaporated to dryness in a rotary evaporator. A brown, solid residue (45 g) remains behind which, according to NMR, consists of the isomeric mixture of 3-(4- methoxy-phenyl)-indenone-2-acetic acid and 6-methoxy-3-phenyl-indenone-2-acetic acid. The isomers can be separated from one another by hot digestion with benzene. After cooling and filtering the suspension with suction, a pure 3-(4-methoxyphenyl)-indenone-2-acetic acid is obtained as orange yellow crystals (25 g).

v) The above reaction product is suspended in about 300 ml of acetic anhydride. After the addition of sodium acetate (20 g), the mixture is refluxed with stirring for 3 hours. A thick product precipitates during cooling. After cooling to room temperature (and briefly also in the refrigerator) the crystalline, orange brown precipitate, which is formed, is filtered off with suction and washed with a little acetic anhydride, until the filtrate no longer is dark brown. Subsequently, it is washed thoroughly with water and dried at 60° C. The product (bright orange colored solid, 25 g) was identified by NMR as being 5-acetoxy-3-methoxy-7H-benzo(c)fluoren-7-one.

vi) The above reaction product is suspended in 400 ml of ethanol and treated with potassium hydroxide (25 g). The reaction mixture is refluxed for 1½hours with stirring, a brilliant deep blue color gradually developing. After cooling, about half the ethanol is evaporated in a rotary evaporator and the residue remaining, together with one liter of water, is heated on the hot plate, until a deep blue solution is formed. The solution is then removed from the hot plate and, while still hot, acidified with concentrated hydrochloric acid while being stirred. A dark violet suspension is formed and cooled to room temperature while being stirred. The suspension is filtered off with suction and washed carefully with water. The material, filtered off, is still very slimy and is sucked dry as well as possible using a membrane pump. After being dried at 60° C., the red-violet product (20 g) was identified by NMR as 5-hydroxy-3-methoxy-7H-benzo(c)fluoren-7-one.

vii) The above reaction product (3 g), together with 1,1-diphenyl-1-propinol (4 g, prepared from benzophenone and sodium acetylide in dimethyl sulfoxide (DMSO) is suspended in about 300 ml of toluene. After the addition of a spatula tip of 4-toluene sulfonic acid, the reaction mixture is refluxed for 1½hours. In the course of the reaction, the naphthol educt, which initially is not very soluble, goes into solution more and more; a red reaction solution is formed. After cooling briefly, the toluene is evaporated under vacuum in a rotary evaporator and the residue dissolved in 40 ml of dichloromethane and subjected to column chromatography on alumina (having a water content of 3%) as a stationary phase and a 2:1 mixture of dichloromethane and hexane as the mobile phase. For the final purification, the product is digested in about 100 ml of methanol and heated a little. After cooling, the suspension formed is filtered off with suction, washed with methanol and dried. The dark red product (3 g) was identified by NMR as 3,3-diphenyl-6-methoxy-13-oxo-indeno(2,1-f)naphtho(1,2-b)pyran.

viii) The above reaction product (2 g) is dissolved with stirring in 50 ml of absolute tetrahydrofuran (THF). To this solution, two equivalents of 2-biphenyl magnesium bromide (prepared from 2-bromobiphenyl and magnesium shavings in a THF solution) are added dropwise and the whole is stirred for one hour at room temperature. Subsequently, it is poured into water and acidified with concentrated hydrochloric acid until the phases are clear and the organic phase is separated. After extracting with water, drying over sodium sulfate and evaporating the solvent in a rotary evaporator, a dark brown oil remains, which is crystallized by the addition of methanol. If the product does not crystallize, it is stirred in an ice bath until crystals precipitate. The suspension is stirred for a few minutes at room temperature, filtered with suction and the filter cake washed with methanol. The resulting beige-colored solid (1 g) was identified by NMR as being 13-(2-biphenyl-3,3-diphenyl-13-hydroxy-6-methoxy-indeno(2,1-f)naphtho(1,2-b)pyran (carbinol 1.

ix) The above reaction product (1 g) is cyclized by the method of R. G. Clarkson, M. Gomberg, J. Am. Chem. Soc. 1930, pg. 2881 ff. by heating it in glacial acetic acid. After the addition of a drop of hydrochloric acid, the solution is heated to the boil for 5 minutes and, while still hot, water is added until the solution becomes cloudy. After cooling, the precipitate is filtered out, washed with water and carefully dried. For a final purification, the solid is dissolved in 40 ml of dichloromethane and subjected to column chromatography on alumina (water content of 3%) as a stationary phase and a 2:1 mixture of dichloromethane and hexane. After digestion with methanol, the pure, light, beige-colored product (0.5 g) is obtained, which was identified by NMR as being spiro-9-fluorene-13'-(3,3-diphenyl-6-methoxy-indeno(2,1-f)naphtho(1,2-b) pyran) (spiro 1).

EXAMPLE 2

The method of Example 1 was used with the exception that, in step vii), the reaction was carried out with 1-(4-methoxyphenyl)-1-phenyl-1-propinol (prepared from 4-methoxybenzophenone and sodium acetylide in DMSO) instead of with 1,1-diphenyl-1-propinol. 6-Methoxy-3-(4-methoxyphenyl)-3-phenyl-13-oxo-indeno(2,1-f)naphtho(1, 2-b)pyran was formed. This is reacted as in Example 1, step viii) with 2-biphenyl magnesium bromide to a product which, according to NMR, is 13-(2-biphenyl)-13-hydroxy-6-methoxy-3-(4-methoxyphenyl)-3-phenyl-indeno(2,1-f) naphtho(1,2-b)pyran (carbinol 2). This is cyclized as in Example 1, step ix) to spiro-9-fluorene-13'-(6-methoxy-3-(4-methoxyphenyl)-3-phenyl-indeno(2,1-f)naphtho(1,2-b) pyran) (spiro 2; 0.7 g), which was identified by NMR.

EXAMPLE 3

The method of Example 2 was used with the exception that, in step viii), the reaction was carried out with 2-phenoxyphenyl magnesium bromide (prepared from 2-bromodiphenyl ether and magnesium in THF solution) instead of with 2-diphenyl magnesium bromide. According to NMR, 13-hydroxy-6-methoxy-3-(4-methoxyphenyl)-13-(2-phenoxyphenyl)-3-phenyl-indeno(2,1-f)-naphtho(1,2-b) pyran) (carbinol 3) is formed. This is cyclized as in Example 1, step ix) to spiro-9-xanthene-13'-(6-methoxy-3-(4-methoxyphenyl)-3-phenyl-indeno(2,1-f)naphtho(1,2-b) pyran) (spiro 3; 0.4 g), which was identified by NMR.

EXAMPLE 4

The method of Example 1 was used with the exception that, in step vii), the reaction was carried out with 1,1-bis (4-methoxyphenyl)-1-propinol prepared from 4,4'-dimethoxybenzophenone and sodium acetylide in DMSO) instead of with 1,1-diphenyl-1-propinol. 3,3-Bis(4-methoxyphenyl)-6-methoxy-13-oxo-indeno(2,-f)naphtho(1, 2-b)pyran) is formed. This is reacted as in Example 1, step viii) with 2-biphenyl magnesium bromide to form a product which, according to NMR, is 13-(2-biphenyl)-3,3-bis(4-methoxyphenyl)-13-hydroxy-6-methoxy-indeno(2,1-f)-naphtho-(1,2-b)pyran) (carbinol 4). This is cyclized as in Example 1, step ix) to form spiro-9-fluorene-13'-(3,3-bis(4-methoxyphenyl)-6-methoxy-indeno(2,1-f)naphtho(1,2-b)pyran) (spiro4; 0.6 g), which was identified by NMR.

EXAMPLE 5

The method of Example 4 was followed with the exception that, in step viii), the reaction was carried out with 2-phenoxyphenyl magnesium bromide instead of with 2-biphenyl magnesium bromide. According to NMR, 3,3-bis(4-methoxyphenyl)-13-hydroxy-6-methoxy-13-(2-phenoxy-phenyl)-indeno(2,1-f)naphtho(1,2-b)pyran) (carbinol 5) is formed. This is cyclized as in Example 1, step ix) to form a product, which was identified by NMR as being spiro-9-xanthene-13'-(3,3-bis(4-methoxyphenyl)-6-methoxy-indeno(2,1-f)naphtho(1,2-b)pyran) (spiro 5; 0.9 g).

EXAMPLE 6

The method was carried out as in Example 4, with the exception that, in step viii), the reaction was carried out with 2-benzylphenyl magnesium bromide (prepared from 2-bromodiphenylmethane and magnesium in THF solution) instead of with 2-biphenyl magnesium bromide. According to NMR, 13-(2-benzylphenyl)-3,3-bis(4-methoxyphenyl)-13-hydroxy-6-methoxy-indeno(2,1-f)naphtho(1,2-b)pyran) (carbinol 6) is formed. This is cyclized, as in Example 1, step ix), into spiro-9-(9,10-dihydroanthracene)-13'-3,3-bis(4-methoxyphenyl)-6-methoxy-indeno(2,1-f)naphtho(1,2-b) pyran) (spiro 6; 0.5 g), which was identified by NMR.

EXAMPLE 7

The method of Example 1 was followed with the exception that, in step vii), the reaction was carried out with 1-(4-(N-morpholinyl)phenyl)-1-phenyl-1-propinol prepared from 4-(N-morpholinyl)-benzophenone (H. Kotsuki, Synthesis 1990, pg. 1145) and sodium acetylide in DMSO) instead of with 1,1-diphenyl-1-propinol. 6-Methoxy-3-(4-N-morpholinyl)phenyl)-3-phenyl-13-oxo-indeno(2,1-f) naphtho(1,2-b)pyran is formed. This is reacted as in Example 1, step viii) with 2-biphenyl magnesium bromide to form a product which, according to NMR, is 13-(-2-biphenyl)-13-hydroxy-6-methoxy-3-(4-(N-morpholinyl) phenyl)-3-phenyl-indeno(2,1-f)naphtho(1,2-b)pyran (carbinol 7). As in Example 1, step ix), this is cyclized to a product, identified by NMR as spiro-9-fluorene-13'-(6-methoxy-3-(4-N-morpholinyl)-phenyl)-3-phenyl-indeno(2,1-f)naphtho(1,2-b)pyran) (spiro 7; 0.4 g).

EXAMPLE 8

The method was carried out as in Example 1, with the exception that, in step vii), the reaction was carried out with 1-(4-dimethylaminophenyl)-1-phenyl-1-propinol (prepared from 4-dimethylamino-benzophenone and sodium acetylide in DMSO) instead of with 1,1-diphenyl-1-propinol. 3-(4-Dimethylaminophenyl)-6-methoxy-3-phenyl- 13-oxo-indeno(2,1-f)naphtho(1,2-b)pyran) is formed. As in Example 1, step viii), this is reacted with 2-biphenyl magnesium bromide to a product which, according to NMR, is 13-(2-biphenyl)-3-(4-dimethylaminophenyl)-13-hydroxy-6-methoxy-3-phenyl-indeno(2,1-f)naphtho(1,2-b)pyran). As in Example 1, step ix), this is cyclized to form spiro-9-fluorene-13'-(3-(4-dimethylaminophenyl)-6-methoxy-3-phenyl-indeno(2,1-f)naphtho(1,2-b)pyran) (spiro 8; 0.6 g), which was identified by NMR.

EXAMPLE 9

The method was carried out as in Example 1, with the exception that, in step vii), the reaction was carried out with 1-(4-dimethylaminophenyl)-1-phenyl-1-propinol (prepared from 4-diphenylaminobenzophenone (B. Staskun, J. Org. Chem. 1968, pg. 3031) and sodium acetylide in DMSO) instead of with 1,1-diphenyl-1-propinol. 3-(4-diphenylaminophenyl)-6-methoxy-3-phenyl-13-oxo-indeno (2,1-f)naphtho(1,2-b)pyran) is formed. As in Example 1, step viii), this was cyclized with 2-biphenyl magnesium bromide into a product which, according to NMR, is 13-(2-biphenyl)-3-(4-diphenylaminophenyl)-13-hydroxy-6-methoxy-3-phenyl-indeno(2,1-f)naphtho(1,2-b)pyran). As in Example 1, step ix), this is cyclized to spiro-9-fluorene-13'-(3-(4-diphenylaminophenyl)-6-methoxy-3-phenyl-indeno(2,1-f)naphtho(1,2-b)pyran) (spiro 9; 0.5 g), which was identified by NMR.

EXAMPLE 10

The method of Example 4 is followed with the exception that, in step i), the reaction is carried out with benzophenone instead of with 4-methoxybenzophenone. After step vii), 3,3-bis(4-methoxyphenyl)-13-oxo-indeno(2,1-f)naphtho(1, 2-b)pyran) is formed. This is reacted, as in Example 1, step viii), with 2-biphenyl magnesium bromide to a product which, according to NMR, is 3,3-bis(4-methoxyphenyl)-13-(2-biphenyl)-13-hydroxy-indeno(2,1-f)naphtho(1,2-b) pyran). As in Example 1, step ix), this is cyclized into spiro-9-fluorene-13'-(3,3-bis(4-methoxyphenyl)-indeno(2, 1-f)naphtho(1,2-b)pyran) (spiro 10; 0.7 g), which was identified by NMR.

EXAMPLE 11

The method of Example 10 was followed, with the exception that, in step vii), the reaction was carried out with 1-(4-(N-morpholinyl)phenyl)-1-phenyl-1-propinol instead of with 1,1-bis(4-methoxyphenyl)-1-propinol. 3-(4-(N-Morpholinyl)phenyl)-3-phenyl-13-oxo-indeno(2,1-f) naphtho(1,2-b)pyran is formed. As in Example 1, step viii), this is reacted with 2-biphenylyl magnesium bromide into a product which, according to NMR, is 13-(2-biphenylyl)-13-hydroxy-3-(4-(N-morpholinyl)phenyl)-3-phenyl-indeno(2, 1-f)naphtho(1,2-b)pyran. As in Example 1, step ix), this is cyclized into spiro-9-fluorene-13'-(3-(4-(N-morpholinyl) phenyl)-3-phenyl-indeno(2,1-f)naphtho(1,2-b)pyran) (spiro 11; 0.6 g), which was identified by NMR.

EXAMPLE 12

The method of Example 4 was followed with the omission of steps i) to vi). As starting material for step vii), 3-bromo-2-hydroxyfluorenone (T. C. Thomas, J. Indian Chem. Soc. 1974, pg. 814)was used instead of 5-hydroxy-3-methoxy-7H-benzo(c)fluoren-7-one. 3,3-Bis(4-methoxyphenyl)-5-bromo-11-oxo-fluoreno(2,1-b)pyran is formed. As in Example 1, step viii), this is reacted with 2-biphenylyl magnesium bromide to form a product, which according to NMR, is 11-(2-biphenyl)-3,3-bis(4-methoxyphenyl)-5-bromo-11-hydroxy-fluoreno(2,1-b)pyran. As in Example 1, step ix), this is cyclized into spiro-9-fluoreno-11'-(3,3-bis(4-methoxyphenyl)-5-bromo-fluoreno(2,1-b)pyran (spiro 12; 0.4 g) which was identified by NMR.

Preparation of the Test Piece:

The respective photochromic dye (500 ppm) is dissolved at room temperature with stirring in the monomer used (TRANSHADE-150 of the Tokuyama company; refractive index: 1.52). After the addition of an initiator of the alkyl peroxyester type (1.5% by weight), the solution is degassed twice and subsequently polymerized using the temperature program recommended by Tokuyama. The glass casting molds are colored black, so that all of the photochromic dye can be incorporated in the matrix in the non-excited state. At the end of the polymerization, the sample pieces are tempered for 2 hours at 100° C.

Determination of Kinetic Values, a*/b* Chromaticities and Longest Wavelength Absorption Maxima:

To determine the brightening rates, the sample pieces prepared are measured in a Zeiss, model PTM II kinetic bench (irradiation with 50 klux in accordance with DIN EN 1836, Item 6.1.3.1.1.). In each case, the illumination time was 15 minutes and the brightening in the dark was 10 minutes. The temperature of the glass is controlled by means of a cuvette, which can be thermostatted. During the illumination and brightening, the transmission, evaluated according to the brightness sensitivity of the human eye Vλ, is recorded at short time intervals. In addition, the PTM II kinetic bench at short time intervals, supplies the a*/b* chromaticity data of the sample pieces in accordance with CIE 1976 as well as, towards the end of the illumination, the UV/VIS spectrum of the darkened sample piece, from which the longest wavelength maxima are determined.

Determination of Yellow Index Value yi and Performance Retention LE:

The yellow index yi is determined in accordance with the ASTM standard D 1925-70. For this purpose, the x/y/z chromaticity data of the sample pieces were determined in accordance with CIE 1931 with the normal type of light C. The greater the yellow index value yi, the greater is the yellowing. This value is particularly informative with respect to the service life test of the sample piece. For this purpose, the sample pieces are illuminated for 50 hours in the SUNTEST CPS rapid illumination equipment of the Heraeus company, equipped with a xenon radiator as well as with a special glass UV filter with a cutoff at 290 nm. The difference in the yellow index values Δyi before and after this xenon test is a measure of the yellowing of the sample piece in the service life test. The performance retention LE is a measure of the depth, to which the sample piece still darkens after the service life test, that is, a measure of the extent to which the photochromic dyes still react.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A photochromic spirofluorenopyran compound corresponding to formula (I):

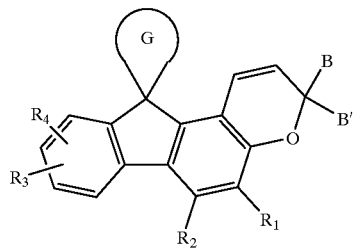

wherein $R_1$ is a substituent selected from the group A consisting of $C_1$ to $C_6$ alkyl, $C_1$ to $C_6$ alkoxy, phenyl, bromine, chlorine and fluorine, and $R_2$, $R_3$ and $R_4$, independently of one another, are the same or different and each represent a substituent selected from group A' consisting of hydrogen and the substituents of group A;

or at least one of the substituent pairs ($R_1$ and $R_2$) and ($R_3$ and $R_4$) independently represents an unsubstituted, monosubstituted or disubstituted benzene or pyridine ring, the substituents of which are selected from group A;

G which is the spiro carbon atom, represents a 5-member to 8-member ring to which at least one aromatic or heteroaromatic ring system is annelated, each said aromatic or heteroaromatic ring system being selected from group E consisting of benzene, naphthalene, phenanthrene, pyridine, quinoline, furan, thiophene, pyrrole, benzofuran, benzothiophene, indole and carbazol, and each said aromatic or heteroaromatic ring system being unsubstituted or having one or two substituents selected from the group A, and B and B', independently of one another, are selected from the following groups a), b), c) and d) wherein
group a) consists of the aryl groups phenyl and naphthyl, which are unsubstituted, monosubstituted, disubstituted or trisubstituted;
group b) consists of the heterocyclic groups pyridyl, furanyl, benzofuranyl, thienyl, benzothienyl and julolidinyl, which are unsubstituted, monosubstituted or disubstituted;
wherein the substituent or substituents of the aryl or heterocyclic groups in the groups a) and b) are selected from the group F consisting of hydroxy, amino, $C_1$ to $C_6$ monoalkylamino, $C_1$ to $C_6$ dialkylamino, mono- and diphenylamino unsubstituted, monosubstituted or disubstituted at the phenyl ring, piperidinyl, N-substituted piperazinyl, pyrrolidinyl, imidazolidinyl, pyrazolidinyl, indolinyl, morpholinyl, carbazolyl, unsubstituted, monosubstituted and disubstituted pyrryl, $C_1$ to $C_6$ alkyl, $C_1$ to $C_6$ alkoxy, bromine, chlorine and fluorine, and
wherein the substituent or substituents on the aromatic and heteroaromatic rings in the group F are selected from the group consisting of $C_1$ to $C_6$ alkyl, $C_1$ to $C_6$ alkoxy, bromine, chlorine and fluorine;
group c) consists of groups having the following structures:

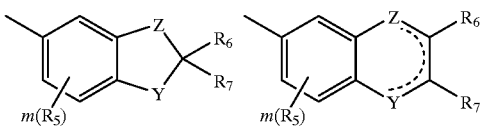

wherein
Y and Z, independently of one another, are selected from the group consisting of O, S, CH, $CH_2$, $NR^N$ in which $R_N$ is $C_1$ to $C_6$ alkyl, $C_1$ to $C_6$ acyl, phenyl or hydrogen;
$R_5$ is selected from the group consisting of hydroxy and the substituents of group A;
m is 0, 1 or 2; and
$R_6$ and $R_7$ are independently selected from the group consisting of hydrogen and $C_1$ to $C_6$ alkyl; and
group d) consists of B and B' together representing an unsubstituted, monosubstituted or disubstituted fluorene-9-ylide group or a saturated hydrocarbon group which is $C_3$ to $C_{12}$ spiro monocyclic, $C_7$ to $C_{12}$ spiro bicyclic or $C_7$ to $C_{12}$ spiro tricyclic; the substituents on the fluorene-9- ylide group being selected from the group A.

2. A photochromic spirofluorenopyran compound according to claim 1, corresponding to the formula (II):

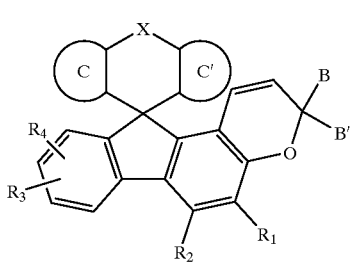

II wherein
$R_1$ to $R_4$, B and B' have the meanings given in claim 1;
X represents a single bond or a linking group selected from the group consisting of —O—; —S—; —($CR_2$)$_n$—in which n is 1, 2 or 3; D=D'in which D and D' are N or CR; and —LL'in which L and L' are O, S, NR, CHR or $CR_2$; R being H, $C_1$ to $C_6$ alkyl or phenyl; L and L' cannot both be O or S at the same time, and C and C' are independently selected from the group E and may each independently have zero, one or two substituents selected from the group A.

3. A photochromic spirofluorenopyran compound according to claim 2, wherein X represents a single bond, and the two ring systems C and C' are bridged by a further linkage, which is in the ortho and ortho' position to the single bond represented by X.

4. A photochromic spirofluorenopyran compound according to claim 3, wherein the further linkage linking the ring systems C and C' in the position ortho and ortho' to the bond represented by X, forms a 4,5-phenanthryl-spiro compound.

5. A photochromic spirofluorenopyran compound according to claim 1, wherein B and B', independently of one another, are selected from the group a) or the group d).

6. A photochromic spirofluorenopyran compound according to claim 5, wherein B and B', independently of one another, represent unsubstituted phenyl or naphthyl, or phenyl or naphthyl monosubstituted by a substituent selected from the group F.

7. A photochromic spirofluorenopyran compound according to claim 1, wherein the substituents represented by B and B' are the same.

8. A photochromic spirofluorenopyran compound according to claim 1, wherein C and C', independently of one another, represent unsubstituted phenyl or naphthyl, or phenyl or naphthyl monosubstituted by a substituent selected from the group A.

9. A photochromic spirofluorenopyran compound according to claim 1, wherein the substitutents represented by C and C' are the same.

10. A photochromic spirofluorenopyran compound selected from the group consisting of:
spiro-9-fluorene-13'-(3,3-diphenyl-6-methoxy-indeno(2,1-f)naphtho(1,2-b)pyran);
spiro-9-fluorene-13'-(6-methoxy-3-(4-methoxyphenyl)-3-phenyl-indeno(2,1-f)-naphtho(1,2-b)pyran);
spiro-9-xanthene-13'-(6-methoxy-3-(4-methoxyphenyl)-3-phenyl-indeno(2,1-f)-naphtho(1,2-b)pyran);
spiro-9-fluorene-13'-(3,3-bis(4-methoxyphenyl)-6-methoxy-indeno(2,1-f)naphtho-(1,2-b)pyran);
spiro-9-xanthene-13'-(3,3-bis(4-methoxyphenyl)-6-methoxy-indeno(2,1-f)-naphtho(1,2-b)pyran);
spiro-9-(9,10-dihydroanthracene)-13'-(3,3-bis(4-methoxyphenyl)-6-methoxy-indeno(2,1-f)naphtho(1,2-b)pyran);
spiro-9-fluorene-13'-(6-methoxy-3-(4-N-morpholinyl)phenyl)-3-phenyl-indeno(2,1-f)-naphtho(1,2-b)pyran);
spiro-9-fluorene-13'-(3-(4-dimethylaminophenyl)-6-methoxy-3-phenyl-indeno(2,1-f)-naphtho(1,2-b)pyran);
spiro-9-fluorene-13'-(3-(4-diphenylaminophenyl)-6-methoxy-3-phenyl-indeno(2,1-f)-naphtho(1,2-b)pyran);
spiro-9-fluorene-13'(3,3-bis(4-methoxyphenyl)-indeno(2,1-f)naphtho(1,2-b)pyran);
spiro-9-fluorene-13'-(3-(4-(N-morpholinyl)phenyl)-3-phenyl-indeno(2,1-f)naphtho-(1,2-b)pyran);
spiro-9-fluorene-11'-(3,3-bis(4-methoxyphenyl)-5-bromo-fluoreno(2,1-b)pyran), and
spiro-9-fluorene-13'-(3,3-bis(4-methoxyphenyl)-5-bromo-benzo(I)fluoreno(2,1-b)pyran).

* * * * *